United States Patent [19]

Koubek

[11] Patent Number: 4,512,951
[45] Date of Patent: Apr. 23, 1985

[54] HYDROGEN PEROXIDE LIQUID FILM STERILIZATION METHOD

[75] Inventor: Edward Koubek, Annapolis, Md.

[73] Assignee: American Sterilizer Company, Erie, Pa.

[21] Appl. No.: 520,146

[22] Filed: Aug. 4, 1983

Related U.S. Application Data

[63] Continuation of Ser. No. 358,435, Mar. 15, 1982, abandoned, which is a continuation of Ser. No. 221,426, Dec. 30, 1980, abandoned.

[51] Int. Cl.³ .............................................. A01N 1/00
[52] U.S. Cl. .................................................... 422/33
[58] Field of Search ........................ 422/27, 28, 29, 33

[56] References Cited

U.S. PATENT DOCUMENTS

| | | | |
|---|---|---|---|
| 3,139,323 | 6/1964 | Shields et al. | 422/27 |
| 3,750,367 | 8/1973 | Barker et al. | 422/28 X |
| 3,854,874 | 12/1974 | Loliger et al. | 422/29 X |
| 3,904,361 | 9/1975 | Egger | 422/27 |
| 3,933,428 | 1/1976 | Egger | 422/28 |
| 4,169,123 | 9/1979 | Moore et al. | 422/28 X |
| 4,169,124 | 9/1979 | Forstrom et al. | 422/33 |
| 4,225,556 | 9/1980 | Lothman et al. | 422/28 |

Primary Examiner—Thomas Wyse
Attorney, Agent, or Firm—Robert D. Yeager

[57] ABSTRACT

A method is provided of hydrogen peroxide sterilization of medical articles whereby there are obtained the advantages of both vapor penetration, especially for such articles as surgical packs, and direct liquid-sterilant article contact, in which a vapor mixture comprising hydrogen peroxide is brought into contact with the article to be sterilized, the article being at a temperature below the dew point or condensation temperature of the vapor mixture, is caused thus to condense as a liquid film on the article, and is revaporized and hence removed from the so-sterilized article.

7 Claims, 1 Drawing Figure

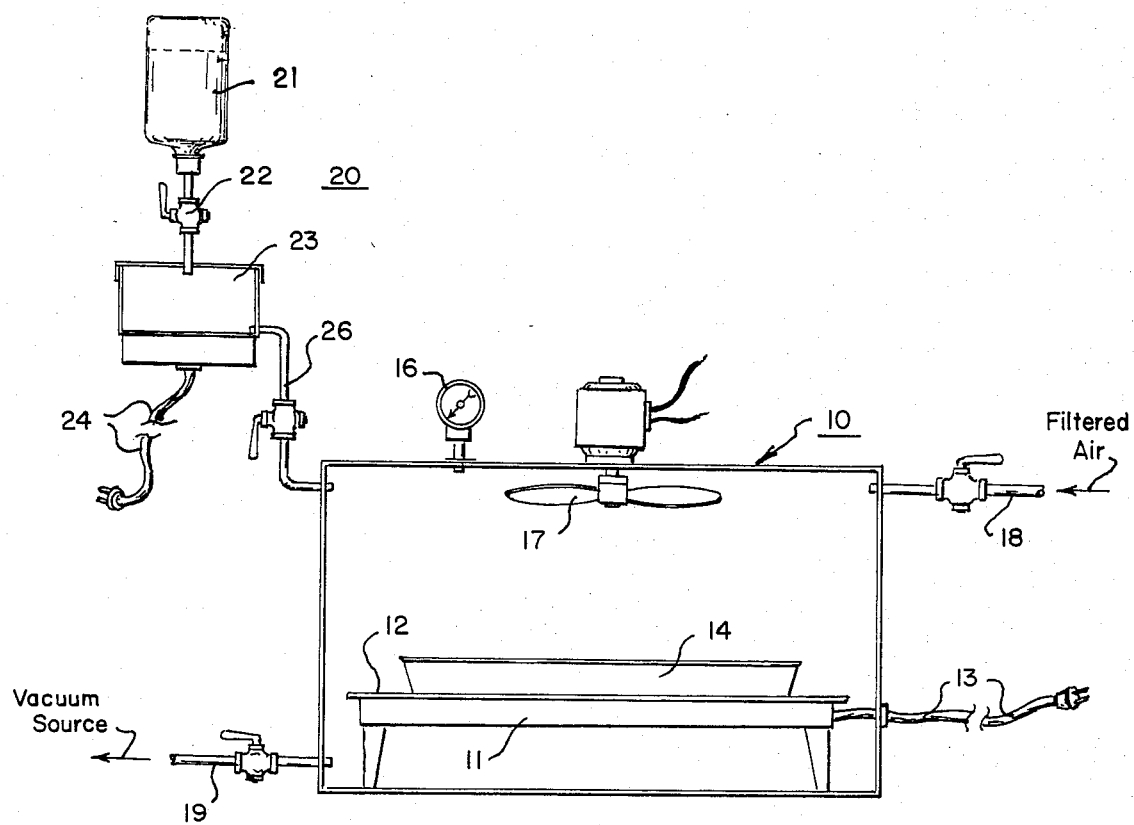

HYDROGEN PEROXIDE LIQUID FILM STERILIZATION METHOD

CROSS REFERENCE TO RELATED APPLICATIONS

This is a continuation of U.S. Ser. No. 358,435, filed Mar. 15, 1982, abandoned which is a continuation of U.S. Ser. No. 221,426, filed Dec. 30, 1980, abandoned.

BACKGROUND OF THE INVENTION

1. Field of the Invention

This invention relates to an improved method of sterilizing articles employed in surgery, treatment, and diagnosis.

2. Description of the Prior Art

It is well known that the dipping of articles into concentrated solutions of hydrogen peroxide (10% to 40%) will sterilize such articles; see, for example, U.S. Pat. Nos. 3,854,874 and 3,904,361. It is also known that hydrogen peroxide vapors will effect such sterilization; see, U.S. Pat. Nos. 4,169,123 and 4,169,124. Reference is particularly made to the latter two patents which compare the bactericidal or sporicidal action of both liquid and gaseous hydrogen peroxide and further note that the sporicidal activity, as recommended by the Food and Drug Administration, of a sterilizing process must assure a probability of less than one organism out of one million surviving the sterilization cycle.

While the dipping of articles to be sterilized in solutions of liquid hydrogen peroxide is effective to reduce bacterial spore concentration to about $10^{-6}$ or better, there are disadvantages to be encountered in this process: (1) dipping objects to be sterilized in a bulk liquid can lead to the contamination of the entire solution and prevent its future use, (2) dipping objects exposes workers and the surrounding environment to the usual hazards of working with fairly large quantities of the sterilant hydrogen peroxide and its attending vapors, and (3) dipped objects may have to be rinsed with sterile distilled water before drying to ensure that any nonvolatile materials present in the sterilization solution will not remain on the object following the required drying step. Inasmuch as hydrogen peroxide is unstable in solution it is necessary to employ stabilizers to control its rate of decomposition. While such deposition of solid stabilizers on the products to be sterilized is avoided in the forementioned U.S. Pat. Nos. 4,169,123 and 4,169,124, the advantage of bringing the articles to be sterilized into positive contact with liquid hydrogen peroxide solutions is not thereby obtained. When, in addition, hydrogen peroxide aerosols are employed (NASA Technical Translation TTF-15, 127, of Fedyayev et al., Virucidal Action of Hydrogen Peroxide Aerosols in Decontamination of Air in an Influenza Nidus, Zhurnal Mikrobiologii, Eipidemologii i Immunobiologii, 9, 137–142 (1972) there is no assurance that the aerosols will not carry with them dispersed particles containing stabilizer components.

In addition, dipping methods introduce the inherent unreliability of individual action in that, for example, articles may not be completely dipped in solution or they may be protected by small air pockets and solution thereby does not contact every surface or penetrate every crevice of the article; or the article may not be immersed for a sufficient period of time in the solution.

The notable sporicidal action of gaseous hydrogen peroxide, as taught in U.S. Pat. Nos. 4,169,123 and 4,169,124 may be explained by the fact that the sterilization chamber preferably is evacuated before introduction of the sterilant. This means that the gaseous sterilant is not impeded by diffusion through air in reaching the articles to be sterilized. Further, intimate contact is possible between the gaseous sterilant and the surface of an article to be sterilized without the interference of air entrapped in interstices adjacent such surface.

Since the sporcidal activity of hydrogen peroxide is chemical in nature, the rate of such (killing) activity is increased by an increase in the concentration of the sterilant at the point of attack. The present invention is directed to accomplishing such an increase in sterilant concentration by creating a liquid hydrogen peroxide condensate in the presence of a vacuum, the liquid being more highly concentrated than the hydrogen peroxide vapor taught in U.S. Pat. Nos. 4,169,123 and 4,169,124. In other words, the present invention may be considered a "dip process" with each "dip" applying a fresh, pure liquid sterilant to an evacuated (air free) surface.

SUMMARY OF THE INVENTION

This invention is directed to improvements in methods for the sterilization of articles in which both the advantages of liquid sterilization and gas sterilization can be obtained. None of the aforementioned disadvantages of liquid dipping sterilization exist in the process of invention and yet the sterilizing impact of the relatively high concentrations of hydrogen peroxide that exist in liquid as compared to gaseous form are brought into liquid-surface contact with the articles to be sterilized. At the same time the substantial advantages of gas sterilization are also obtained especially in the high penetration of the particular articles which results in unusually high sporicidal action, for example as cited in U.S. Pat. No. 4,169,124, whereby sporicidal activity in the order of magnitude of assuring the survival of less than one organism out of one million is obtained.

In the method of invention uniformly vaporized mixed hydrogen peroxide-water vapors are delivered at uniform intervals into a closed sterilizer zone, which has been evacuated prior to the vapor introduction; articles to be sterilized resting in a container in the said zone if necessary are cooled prior to the introduction of the vapor (or are cooled by the evacuation of air from the sterilizing zone) to a temperature below the dew point of the entering vapors, whereby the vapors penetrate all the interstices of the said articles, contact all surfaces thereof, and by condensing deposit a film of liquid on all such cool surfaces; and the liquid film is subsequently evaporated and swept out of the chamber by the introduction of filtered air which will act to strip the liquid film from the sterilized articles, the said articles being preferably warmed to aid in driving off the said liquid film.

Apparatus for carrying out the method of the invention while specially adapted to the method can be of widely varying sophistication and it is contemplated that commercial apparatus will be actuated by set timer switches or the like. After the sterilizer is loaded, a single actuator button can be pressed and conventional sequentially timed apparatus will carry out the entire sterilization cycle.

BRIEF DESCRIPTION OF THE DRAWING

The single FIGURE is a side elevational view of means for carrying out the method of the invention, in which FIGURE the means are shown to be manually operated in order to permit simplification of description of the novel method.

DETAILED DESCRIPTION OF THE PREFERRED EMBODIMENTS

A sterilizer 10 is shown with its front section containing a door (not shown) removed. Contained within the sterilizer section is an instrument table 11 having means for heating or cooling its base 12 such means being symbolized by the electrical cord 13. Resting on the instrument table 11 is a container 15 in which are placed materials emanating from surgical or medical procedures and which require sterilization in high degree before reuse. The sterilization chamber is provided with a pressure gauge 16 and a fan 17. A supply of filtered air is provided to the chamber 10 by valved line 18 and vacuum may be imposed upon the sterilization chamber 10 by withdrawal of air or vapors through valved line 19. Equipment for vaporization of hydrogen peroxide solutions 20 consists of a supply flask 21, a valved supply line 22, and an evaporator 23 having a source of heat symbolized by electrical line 24. Means are provided for releasing the generated hydrogen peroxide vapor through connecting valved line 26.

In operation of the foregoing apparatus according to the method of the invention an aqueous concentrated solution, (having for example from about 10% to 40% of hydrogen peroxide) is permitted to flow from the storage or supply vessel 21 in small volume increments through the valved supply line 22 into the vaporization chamber 23.

At the same time the sterilization chamber 10 is evacuated by pump means (not shown) through vacuum line 19 the valved lines 18 and 26 being closed during this operation. The increment of hydrogen peroxide solution in the vaporizer 23 is heated by means 24 and vapors so produced are allowed to flow through valved line 26, by opening the valve therein, into the sterilization chamber 10.

Importantly the articles (not shown) in the container 14 in the sterilization chamber are maintained at a temperature below the dew point of the hydrogen peroxide vapors entering the said chamber. This is basically accomplished by maintaining the evacuated ambient low pressure air in the chamber at a temperature only slightly above, if at all, of the articles to be sterilized and/or by circulating cooling medium in the base 12 of instrument table 11. Accordingly hydrogen peroxide vapors will condense on the entire surfaces of the articles within the container 14. The valved line 26 will thereupon be closed and the sterilization chamber will be maintained under stable conditions for a selected period of sterilization time. Thereafter valved line 18 and valved line 19 are opened and filtered aseptic air is caused to flow through the chamber 10 to evaporate from the surface of articles being sterilized the liquid film that had been maintained thereon. These vapors are caused to escape through the open valved line 19. Evaporation of the film of liquid on the articles that have been sterilized is augmented by heat delivered by device 13 and associated heating elements (not shown) in the said base 12. The fan 17, the blades of which are mounted in the upper area of the sterilization chamber free of contact with the sterilization articles can be used either to ensure uniform distribution of inflowing hydrogen peroxide vapors (in which case the operation of the fan blades will be at a low velocity) or it may be used at high velocity to aid in the vaporization of the film of liquid on the articles that have been sterilized.

The temperature of operation within the sterilization chamber and especially of the articles to be sterilized will be basically governed by the dew point of the particular concentration of hydrogen peroxide in the vapors introduced into the chamber. Temperatures generally within the range of about 15° C. to 55° C. effect sterilization of most articles in a period of hours, the temperature primarily being selected so that a film of liquid forms on the articles while nevertheless the inflowing vapors are not so rapidly condensed but what in the gaseous form they can and do penetrate all the interstices of the said articles.

A 30 percent by weight solution of hydrogen peroxide is heated in the vessel 23 to a temperature of about 130° F. thereby producing a vapor containing about 2 to 2.5 percent by weight of hydrogen peroxide. Air in sterilization chamber 10 is evacuated therefrom to an absolute pressure of between 2 and 4 inches of Hg. The aforesaid hydrogen peroxide vapor is then permitted to flow into the chamber the walls of which are maintained at or near 100° F. and into contact with articles to be sterilized at normally about 70° F., these articles having just been placed in the chamber at the usual ambient room temperature or at slightly cooler temperatures. That portion of the 2 to 2.5 percent hydrogen peroxide vapor which comes in contact with the said articles will be cooled to about 70° F., a temperature below the dew point of the vapor, and a condensation of a liquid film will result, the condensate liquid containing about 37 percent by weight of hydrogen peroxide. Vapor is allowed to flow into the sterilization chamber until equilibrium pressure is established, the condensation of liquid on the articles to be sterilized in the meantime raising the surface temperature of the said articles, it may be until they reach an equilibrium temperature with the vapor in the chamber. The sterilization zone is then closed and stable conditions are maintained therein for a period which may vary widely from several minutes to several hours with different materials to be sterilized and different microorganism to be killed, until conventional laboratory monitoring means shows complete kill to be obtained. Microorganisms commonly employed in such test procedures are *Bacillus subtilis* spores, being highly resistant to sterilization.

Actual temperatures and liquid and vapor concentrations can be varied within the limits of about 100° to 300° F. in the vaporization chamber, 6% to 70% concentration of hydrogen peroxide in the aqueous solution in the vaporizing zone (preferably 30 to 70 percent) and from 50° to 200° F. original temperature in the sterilization zone.

What is claimed is:

1. A method of liquid-contact sterilization which comprises:

vaporizing from an aqueous solution of hydrogen peroxide a gaseous vapor consisting of hydrogen peroxide and water vapor;

passing the said gaseous vapor into an evacuated sterilization zone and into contact therein with an article to be sterilized;

maintaining the article at a temperature below the dew point of the entering vapor so that aqueous hydrogen peroxide solution is condensed out of that said vapor in contact with the said article as a layer of liquid thereon; and maintaining the said film of liquid on the article for a predetermined period to effect sterilization of the article.

2. A method of liquid sterilization which comprises:

vaporizing from an aqueous solution of hydrogen peroxide a mixed gaseous vapor consisting of hydrogen peroxide and water vapor free of solid contaminates which may exist in the said solution and passing the said vapor into an evacuated sterilization zone and therein into contact with an article to be sterilized whereby the vapor penetrates the interstices of the said article;

maintaining the article at a temperature below the dew point of the entering vapor so that hydrogen peroxide solution is condensed out of said vapor as a layer of liquid on the said article;

maintaining the said film of liquid on the article for a predetermined period to effect sterilization of the article; and vaporizing the hydrogen peroxide solution from the surface of the article and removing the so-sterilized-article from the sterilization zone.

3. The method of claim 2 in which the mixed vapor of hydrogen peroxide and water is passed into the sterilization zone and into contact with the article to be sterilized until the heat of condensation of the vapor raises the temperature of the surface of said article to equilibrium temperature with that of the vapor.

4. The method of claim 1 in which there is employed an aqueous solution of hydrogen peroxide in concentration between 6% and 70% by weight of solution.

5. The method of claim 1 in which the hydrogen peroxide is vaporized at a temperature between 100° and 300° F.

6. The method of claim 5 in which the temperature in the sterilization zone is upon introduction of the said hydrogen peroxide vapor mixture at a temperature between 50° and 200° F. but is lower than the vaporization temperature utilized.

7. The method of claim 1 in which so-formed vapor of hydrogen peroxide and water is introduced into the sterilization zone, articles to be sterilized are placed in the sterilization zone, thereafter closed to ambient air, at a temperature substantially below the temperature of the introduced said vapor, and the sterilization zone is warmed to a temperature above the temperature of the said article but below the temperature of the introduced vapor.

* * * * *